(12) United States Patent
Hu et al.

(10) Patent No.: US 10,398,127 B2
(45) Date of Patent: Sep. 3, 2019

(54) SYSTEM, METHOD AND FEEDING DEVICE FOR REMOTE PET MONITORING AND FEEDING

(71) Applicant: SOCIÉTÉ DES PRODUITS NESTLÉ S.A., Vevey (CH)

(72) Inventors: Bao Zhong Hu, Shanghai (CN); Werner Bauer, Lutry (CH); Ruguo Hu, Ningho (CN)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 477 days.

(21) Appl. No.: 14/909,595

(22) PCT Filed: Aug. 7, 2014

(86) PCT No.: PCT/IB2014/063778
§ 371 (c)(1),
(2) Date: Feb. 2, 2016

(87) PCT Pub. No.: WO2015/022608
PCT Pub. Date: Feb. 19, 2015

(65) Prior Publication Data
US 2016/0192620 A1    Jul. 7, 2016

Related U.S. Application Data

(60) Provisional application No. 61/865,295, filed on Aug. 13, 2013.

(51) Int. Cl.
*A01K 5/02* (2006.01)
*A01K 5/01* (2006.01)
(Continued)

(52) U.S. Cl.
CPC .......... *A01K 5/0283* (2013.01); *A01K 5/0114* (2013.01); *A01K 29/005* (2013.01); *A61B 5/01* (2013.01); *A61B 5/02055* (2013.01)

(58) Field of Classification Search
CPC .................................................. A01K 5/0283
See application file for complete search history.

(56) References Cited

U.S. PATENT DOCUMENTS

| 8,100,084 B1 * | 1/2012 | Abramson ........... A01K 5/0283 |
| | | 119/51.02 |
| 2006/0011144 A1 | 1/2006 | Kates |
| | (Continued) | |

FOREIGN PATENT DOCUMENTS

| CA | 2634452 | 7/2007 |
| CN | 1210669 A | 3/1999 |
| | (Continued) | |

OTHER PUBLICATIONS

International Search Report and Written Opinion to PCT/IB2014/063778 dated Jan. 23, 2015.

*Primary Examiner* — Kristen C Hayes

(57) ABSTRACT

A system, a feeding device, and a method enable a terminal device of a pet owner to directly and/or indirectly communicate with the feeding device. The feeding device can monitor and/or feed the pet. For example, components of the feeding device, along with a sensor worn by the pet and in communication with the feeding device, can monitor the pet. A cloud database may compile and may perform an analysis of health and wellness information and food consumption data sent from the feeding device and may communicate with the terminal device of the pet owner bidirectionally. The analysis can use data from a consumer-club of pets to provide best service. The feeding device can also communicate with the terminal device of the pet owner bidirectionally, either directly using one or more wireless connections or indirectly using the cloud database.

5 Claims, 4 Drawing Sheets

(51) Int. Cl.
   *A01K 29/00*      (2006.01)
   *A61B 5/01*       (2006.01)
   *A61B 5/0205*     (2006.01)

(56) References Cited

U.S. PATENT DOCUMENTS

| | | | | |
|---|---|---|---|---|
| 2007/0137584 | A1* | 6/2007 | Travis | A01K 5/02 |
| | | | | 119/51.02 |
| 2008/0314335 | A1* | 12/2008 | Kates | A01K 15/02 |
| | | | | 119/720 |
| 2009/0095223 | A1* | 4/2009 | Szutu | A01K 5/0114 |
| | | | | 119/51.11 |
| 2010/0263596 | A1* | 10/2010 | Schumann | A01K 5/0114 |
| | | | | 119/51.02 |
| 2010/0289639 | A1 | 11/2010 | Gibson | |
| 2011/0139076 | A1* | 6/2011 | Pu | A01K 5/0114 |
| | | | | 119/51.02 |
| 2011/0192351 | A1 | 8/2011 | Jackson | |
| 2012/0227668 | A1 | 9/2012 | Aycock | |
| 2013/0092099 | A1 | 4/2013 | Hardi | |
| 2016/0029592 | A1* | 2/2016 | Springer | A01K 5/0225 |
| | | | | 119/51.11 |

FOREIGN PATENT DOCUMENTS

| | | |
|---|---|---|
| CN | 101014240 A | 8/2007 |
| JP | 2004212544 | 7/2004 |
| JP | 200573589 A | 3/2005 |
| RU | 2474110 C1 | 2/2013 |
| WO | 2007129917 | 11/2007 |
| WO | 2010033197 | 3/2010 |
| WO | 2011130538 A2 | 10/2011 |

* cited by examiner

SYSTEM, METHOD AND FEEDING DEVICE FOR REMOTE PET MONITORING AND FEEDING

CROSS REFERENCE TO RELATED APPLICATIONS

This application is a national stage application under 35 USC § 371 of PCT/IB2014/063778 filed on Aug. 7, 2014 and claims priority to U.S. Provisional Application No. 61/865,295 filed Aug. 13, 2013, the disclosures of which are incorporated herein by this reference.

BACKGROUND

The present disclosure generally relates to a system, a method and a feeding device that enable a pet owner to remotely monitor and feed a pet. More specifically, the present disclosure relates to a system comprising a feeding device and a cloud database that communicate with a terminal device of the pet owner.

Pets are often considered a family member, and typically their health and wellness are of great importance to their owner. However, monitoring pet health and wellness at all times and providing food in a systematic, recommended and pre-arranged way is difficult and inconvenient for most pet owners. For example, pet owners are increasingly away from home for work and other purposes, and pet owners who are away from home do not know the current condition of their pet and do not have the ability to control the specific amount of food available for their pet at a given time.

Pet feeding dishes are commercially available; however, these dishes typically do not address the problem of providing food to a pet over an extended period of time. For example, most feeding dishes lack a mechanism for providing numerous successive meals in the absence of the pet owner. Although some known feeding devices have different functions for pet training, providing food, water feeding and the like, these devices only have basic programming functions and only perform one-way control of the feeding system i.e. the input of the user on an interface integral with the device. Moreover, these feeding devices do not remedy the problem that pets may change their eating habits when the pet owner is not present at the home, especially for lengthy absences. For example, some pets may eat less or not at all when the pet owner is absent. Thus these devices do not fulfill the increasing needs of pet and their owners or enable interaction between them.

SUMMARY

The present disclosure provides a system, a feeding device, and a method that enable a terminal device of a remotely located pet owner to directly and/or indirectly communicate with the feeding device. The feeding device can monitor and/or feed the pet. For example, components of the feeding device, along with a sensor worn by the pet and in communication with the feeding device, can monitor the pet. A cloud database may compile and may evaluate health and wellness information and food consumption data sent from the feeding device and may communicate with a terminal device of the pet owner bidirectionally. The feeding device can also communicate with the terminal device of the pet owner bidirectionally, either directly using one or more wireless connections or indirectly using the cloud database.

Accordingly, in an embodiment, the present disclosure provides a system comprising: a portable sensor that obtains a measurement related to health of a pet; and a feeding device to which the sensor connected, the feeding device receiving measurements from the sensor, the feeding device comprising a scale, a container, and a dispenser that dispenses pet food from the container into a bowl associated with the scale, the feeding device generating feeding consumption data, and the feeding device further comprises an internet connection.

In a related embodiment, the system further comprises a database remotely located relative to the feeding device, and the feeding device transmits the measurements and the feeding consumption data to the database through the internet connection. The database can be configured to perform an analysis of the measurement and the feeding consumption data using information stored in the database, and the information stored in the database is selected from the group consisting of scientific information, previously compiled data for the pet, previously compiled data for other pets that are the same type of pet, and a combination thereof. The database can host a website that provides at least a portion of the measurement, the feeding consumption data, and results of the analysis, and the database is configured to transmit a command to the feeding device in response to user input into the website.

In a related embodiment, the measurement is selected from the group consisting of a distance moved by the pet over a time period, a real-time body temperature of the pet, a real-time blood pressure of the pet, a real-time heart rate of the pet, and combinations thereof.

In another embodiment, a method is provided. The method comprises automatically measuring pet food consumption locally to generate pet food consumption data; automatically obtaining real-time pet health and wellness measurements locally; and transmitting the pet food consumption data and the real-time health and wellness measurements from a feeding device to a remotely located device using an internet connection.

In a related embodiment, at least a portion of the pet food consumption data and the real-time health and wellness measurements are transmitted to a remotely located database that uses stored information to perform an analysis of the pet food consumption data and the real-time health and wellness measurements. The method can further comprise automatically transmitting a message from the database based on the analysis. The message can be transmitted from the database to a terminal device remotely located relative to the feeding device and the database. The message can be transmitted from the database to the feeding device.

In a related embodiment, the method further comprises using the internet to transmit a command to the feeding device, and the feeding device dispenses an amount of pet food in response to the command. The command can identify the amount of pet food. The feeding device can dispense the pet food substantially concurrently to receipt of the command by the feeding device.

In another embodiment, a system is provided. The system comprises a plurality of computers that automatically receive data regarding pet health and wellness and provide the data to a database, and the database allows users to access the data for pets that are the same type of pet relative to each other.

In a related embodiment, the system further comprises a feeding device that transmits new data that is associated with a pet to the database, and the database uses the data for the pets that are the same type of pet to perform an analysis of the new data.

In a related embodiment, the data comprises measurements are selected from the group consisting of a distance moved over a time period, a real-time body temperature, a real-time blood pressure, a real-time heart rate, and combinations thereof.

In a related embodiment, the data comprises feeding consumption data comprising times that pet food was consumed and, for each of the times, an amount consumed.

In a related embodiment, the same type of pet is determined at least partially using a criterion selected from the group consisting of pet species, pet breed, pet age, pet weight, and combinations thereof.

In another embodiment, a feeding device is provided. The feeding device comprises: a scale connected to a processor to generate pet food consumption data; a first communication module connected to the processor and configured to receive real-time pet health and wellness measurements from a local sensor; a second communication module connected to the processor and configured to obtain an internet connection by which the pet food consumption data and the real-time pet health and wellness measurements are transmitted; and a dispenser connected to the processor and configured to dispense pet food in response to a command received by the second communication module.

In a related embodiment, the feeding device comprises an infrared sensor connected to the processor.

In a related embodiment, the feeding device comprises a camera that is connected to the processor and captures at least one of pictures and video that are transmitted by the second communication module using the internet connection.

In a related embodiment, the feeding device comprises a speaker that plays audio in response to a message received by the second communication module.

An advantage of the present disclosure is to monitor the activity and health of a pet and use this information to feed the pet according to the best needs of the pet.

Another advantage of the present disclosure is to enable interaction of a remotely located pet owner with the pet, identify the feeding needs of the pet, and feed the pet based on scientific feeding rules and past data about the pet.

Still another advantage of the present disclosure is to feed a pet based at least partially on programming by the owner on-site, remotely, preset or real time.

Yet another advantage of the present disclosure is to locally collect data regarding pet activity and health conditions using a sensor; send the data from the sensor to the feeding device; and then send the data from the feeding device to a cloud database and/or a remotely located terminal device.

An additional advantage of the present disclosure is to use scientific knowledge to remotely analyze data regarding pet activity and health conditions and then send an appropriate command to the feeding device to guide the most suitable feeding of the pet in terms of food type, quantity and feeding time.

Another advantage of the present disclosure is to use a unique interface or mechanism between man, animal and machine.

Still another advantage of the present disclosure is to form a consumer-club of pets to provide best service.

Yet another advantage of the present disclosure is to maintain individual health and wellness data, an activity profile and an eating profile of each pet.

Still another advantage of the present disclosure is to use a customized feeding program to achieve health and wellness of a pet.

Yet another advantage of the present disclosure is to enable a remotely located pet owner to obtain real-time pet health and wellness data.

An additional advantage of the present disclosure is to enable a remotely located pet owner to make feeding decisions regarding a pet and have the feeding decisions implemented by a local feeding device that receives a command from the terminal device of the pet owner.

Another advantage of the present disclosure is to encourage a pet to eat by playing a pre-recorded voice clips to bring relaxation and pleasant enjoyment to the pet.

Still another advantage of the present disclosure is to enable a remotely located pet owner to talk with the pet using a telephone wirelessly connected to a feeding device.

Yet another advantage of the present disclosure is to enable a pet owner to video chat with the pet.

An additional advantage of the present disclosure is to enable a remotely located pet owner to select a type of pet food to be dispensed by a local feeding device.

Another advantage of the present disclosure is to enable a remotely located pet owner to dispense water from a local feeding device.

Additional features and advantages are described in, and will be apparent from, the following Detailed Description and the Figures.

DETAILED DESCRIPTION

Figure 1:
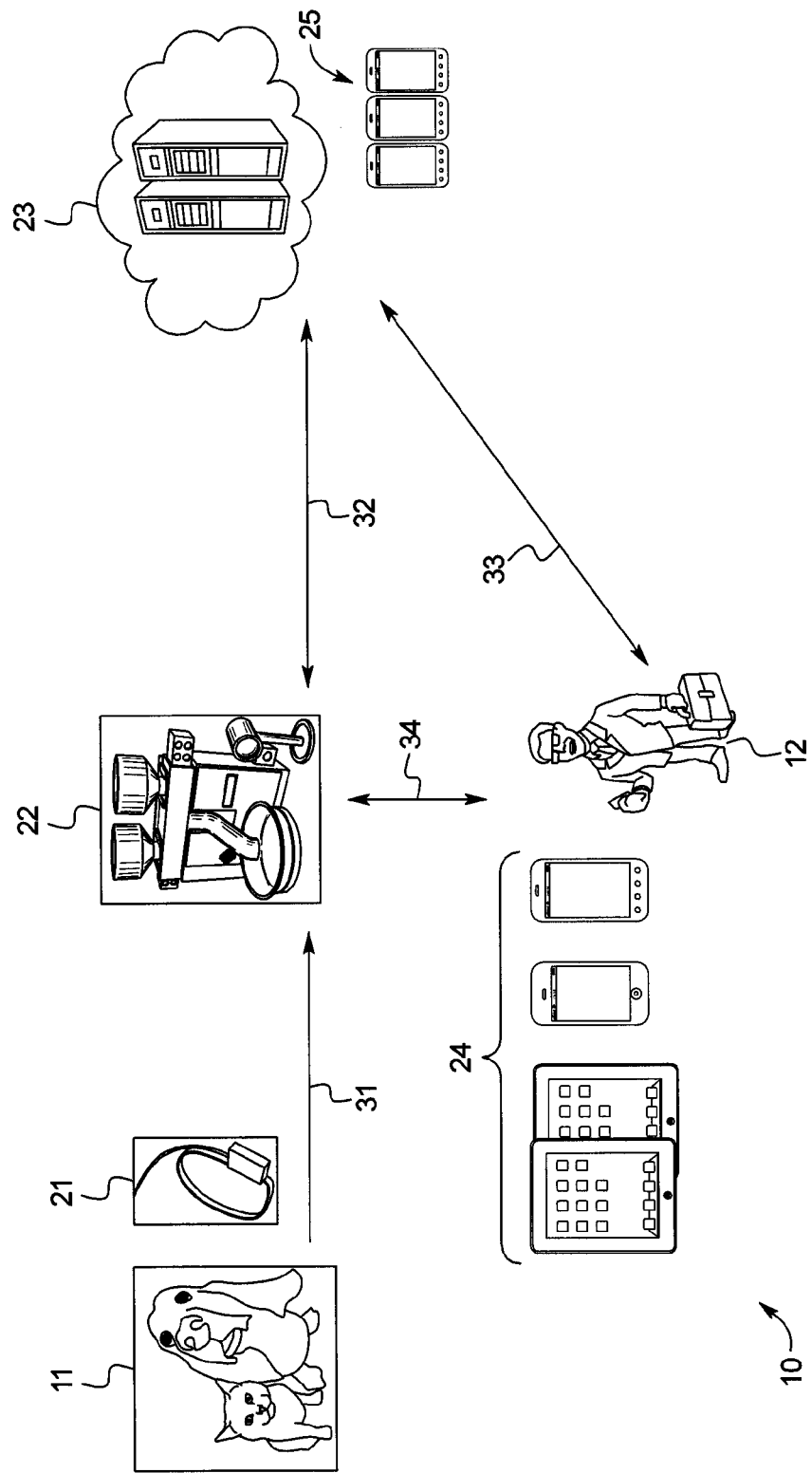
FIG. 1 illustrates an embodiment of a pet monitoring and feeding system provided by the present disclosure.

The term "cloud database" means the hardware (e.g., a computer) and/or the software (e.g., a computer application) that receives, stores, processes and delivers content that can be accessed through the internet, for example, using a website hosted by the cloud database and/or a web server associated with the cloud database.

The term "pet" means any animal which may be monitored and fed. The pet can be an avian, bovine, canine, equine, feline, hicrine, lupine, murine, ovine, or porcine animal. The pet can be any suitable animal, and the present disclosure is not limited to a specific pet animal. The term "companion animal" means a dog or a cat.

The term "pet food" and "food" mean any composition which may be consumed by a pet. In an embodiment, the pet food may be water.

The terms "remotely" and "locally" are in reference to the environment in which the pet is located. Preferably "locally" refers to a domestic or in-home environment, but the present disclosure is not limited to a specific location in which the pet is located.

The term "automatically" means without user input being necessary. An "automatically" performed operation can comprise one or more actions by the corresponding device, but each of the actions is performed without a requirement of user input.

The term "single package" means that the components of a kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof. A single package may be containers of individual components physically associated such that they are considered a unit for manufacture, distribution, sale, or use.

The term "virtual package" means that the components of a kit are associated by directions on one or more physical or virtual kit components instructing the user how to obtain the other components, e.g., a bag or other container containing one component and directions instructing the user to go to a website, contact a recorded message or a fax-back service, view a visual message, or contact an instructor to obtain instructions on how to use the kit or safety or technical information about one or more components of a kit.

As used herein and in the appended claims, the singular form of a word includes the plural, and vice versa, unless the context clearly dictates otherwise. Thus, the references "a," "an" and "the" are generally inclusive of the plurals of the respective terms. For example, reference to "a measuring device" or "a method" includes a plurality of such "measuring devices" or "methods." Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" also is a disclosure of embodiments "consisting essentially of" and "consisting of" the disclosed components. Where used herein, the term "examples," particularly when followed by a listing of terms, is merely exemplary and illustrative, and should not be deemed to be exclusive or comprehensive.

The present disclosure is generally directed to a system, a method and a feeding device that enable a pet owner to remotely monitor and feed a pet. For example, the remote pet monitoring and feeding system can use the internet to provide real-time data regarding pet health, pet desire for food, and an amount of pet food consumed; and can enable the pet owner to remotely direct distribution of pet food into the feeding bowl. A remote web server, such as a cloud database, can analyze the real-time data and, based on the analysis, make feeding decisions and/or provide suggestions to the pet owner. The pet owner can easily connect to the web server by accessing a website.

In an embodiment illustrated in FIG. 1, the present disclosure provides a remote pet monitoring and feeding system 10 (hereafter "the system 10") that enables a pet owner 12 to monitor and feed a pet 11. The system 10 comprises a sensor 21, and preferably the sensor 21 is portable such that the sensor 21 can be worn by the pet 11. For example, the sensor 21 can be a component of a collar worn by the pet 11 and/or may be configured to be attached to a collar worn by the pet 11.

The sensor 21 can automatically obtain real-time health and wellness measurements regarding the pet 11. For example, the sensor 21 can measure a distance moved by the pet 11 over a time period. As another example, the sensor 21 can measure real-time body conditions of the pet 11, such as the real-time body temperature of the pet 11, the real-time blood pressure of the pet 11, and/or the real-time heart rate of the pet 11. In this regard, the sensor 21 can comprise at least one of a motion sensor, a GPS module, a temperature sensor, a blood pressure sensor or a heart rate monitor. The sensor 21 can use a wireless connection 31 to communicate with the feeding device 22 such that the sensor 21 transmits the real-time health and wellness measurements regarding the pet 11 to the feeding device 22.

The system 10 further comprises a feeding device 22 that comprises a feeding bowl for holding pet food and a scale associated with the feeding bowl. As discussed in detail hereafter, the feeding device 22 can dispense an amount of pet food stored by the feeding device 22. The feeding device 22 can be set to operate in manual mode in which the feeding device 22 only dispenses pet food in response to manual input on the feeding device 22, for example user input on an input device integral with the feeding device 22. The feeding device 22 can be set to operate in programmable mode in which the feeding device 22 dispenses pet food according to a feeding program and/or remotely generated commands. The feeding program and/or the remotely generated commands can specify a feeding parameter that is at least one of a day, a time, a type of pet food, or an amount.

The feeding device 22 can automatically determine the amount of pet food consumed by the pet 11 over a time period by determining the decrease in weight of the feeding bowl over the time period and can generate corresponding food consumption data. The processor 224 can automatically generate eating desire data based on how often the pet 11 approaches the feeding device 22, such as by using an infrared sensor. In an embodiment, the pet owner 11 can purchase the sensor 21 with the feeding device 22 as a kit, such as a single package or a virtual package.

The feeding device 22 can use a wireless connection 32 to automatically transmit the real-time health and wellness measurements received from the sensor 21 to a cloud database 23 that comprises a web server. The feeding device 22 can transmit the real-time health and wellness measurements to the cloud database 23 as the feeding device 22 receives the measurements and/or at predetermined time intervals. The feeding device 22 can use the wireless connection 32 to transmit the food consumption data and the eating desire data to the cloud database 23. The wireless connection 34 can enable bidirectional communication; for example, the cloud database 23 can use the wireless connection 34 to send inquiries and/or commands to the feeding device 22. The wireless connection 32 can be an internet connection.

Alternatively or additionally, the feeding device 22 can use a wireless connection 34 to automatically transmit the real-time health and wellness measurements received from the sensor 21 to a terminal device 24 of the pet owner 12. The feeding device 22 can transmit the real-time health and wellness measurements to the terminal device 24 as the feeding device 22 receives the measurements and/or at predetermined time intervals. The feeding device 22 can use the wireless connection 34 to transmit the food consumption data and/or the eating desire data to the terminal device 24 of the pet owner 12. The wireless connection 34 can enable bidirectional communication; for example, the terminal device 24 can use the wireless connection 34 to send inquiries and/or commands to the feeding device 22. The terminal device 24 of the pet owner 12 can be at least one of a mobile telephone, such as a smartphone; a laptop computer; a desktop personal computer; a tablet; or a personal digital assistant. The wireless connection 34 can be an internet connection.

The cloud database 23 can automatically analyze the real-time health and wellness measurements, the eating desire data and the food consumption data received from the feeding device 22. In an embodiment, the cloud database 23 can generate a pet activity profile from the distances moved by the pet 11 as determined by the sensor 23. As a result of analysis, the cloud database 23 can provide a customized feeding program. For example, the cloud database 23 can generate a customized feeding program and/or adjust a previously established feeding program. The feeding program can specify a plurality of feedings, and each feeding can be associated with a feeding parameter that is at least one of a day, a time, a type of pet food, or an amount. In an embodiment, the customized feeding program can be based at least partially on one or more of the distance moved by the pet 11 over a time period, the real-time body temperature of the pet 11, the real-time blood pressure of the pet 11, or the real-time heart rate of the pet 11.

The analysis can also use information stored in the cloud database 23, and the customized feeding program can be based at least partially on the stored information. The stored information can comprise scientific knowledge, such as scientific knowledge associated with the type of pet corresponding to the pet 11, and the scientific knowledge can comprise scientific feeding rules. The type of pet can comprise the species, such as dog or cat; the breed of the pet; the age of the pet; and/or the weight of the pet. Additionally or alternatively, the stored information can comprise previously compiled data for the pet 11, for example previous health and wellness measurements, food consumption data, and/or eating desire data specifically associated with the pet 11.

Feeding commands based on the customized feeding program can be automatically sent from the cloud database 23 to the feeding device 22 without input from the terminal device 24 of the pet owner 12. Alternatively or additionally, feeding recommendations based on the customized feeding program can be automatically sent from the cloud database 23 to the terminal device 24 of the pet owner 12. Each of the commands or recommendations can specify a feeding parameter that is at least one of a day, a time, a type of pet food, or an amount. The feeding device 22 can execute the commands by dispensing pet food according to the command. User input on the terminal device 24 may accept the recommendation, and in response to acceptance of the recommendation the feeding device 22 can execute the recommendation by dispensing pet food according to the recommendation. The acceptance of the recommendation can be transmitted directly from the terminal device 24 to the feeding device 22 or indirectly through the cloud database 23.

The cloud database 23 can use a wireless connection 33 to communicate with the terminal device 24 of the pet owner 12. For example, the cloud database 23 can use the wireless connection 33 to provide the real-time health and wellness measurements, the food consumption data, and results of analysis thereof to the terminal device 24 of the pet owner 12. The cloud database 23 can use the wireless connection 33 to provide the feeding recommendations to the terminal device 24. The cloud database 23 can use text messages, SMS messages, voicemail messages, emails, and the like to communicate with the terminal device 24. In an embodiment, the terminal device 24 of the pet owner 12 can obtain the real-time health and wellness measurements, the food consumption data, and results of analysis thereof by accessing the internet, such as by accessing a website hosted by the cloud database 23.

The wireless connection 34 can enable bidirectional communication; for example, the cloud database 23 can use the wireless connection 33 to receive inquiries and/or commands from the terminal device 24 of the pet owner 12. The wireless connection 33 can be an internet connection. The cloud database 23 can use the wireless connection 33 to provide a website to the terminal device 24 and/or receive input from the terminal device 24 through the website.

As an example of functionality of the cloud database 23, the cloud database 23 can provide a summary of the food consumption, such as the quantity consumed each day for a time period, such as the previous thirty days. Thus the pet owner 12 can know the pet feeding history despite the pet owner 12 not being present at the location of the feeding device 22. The cloud database 23 can store the summaries of the food consumption for later reference by the pet owner 12 and/or later use when the cloud database 23 analyzes the health and wellness measurements, the eating desire data, and the food consumption data.

As another example of functionality of the cloud database 23, the cloud database 23 can send a warning message to the pet owner 12 when the pet food is not consumed for a time period that exceeds a predetermined threshold or when the amount of pet food consumed is less than a predetermined threshold over a preestablished time period. As yet another example of functionality of the cloud database 23, the cloud database 23 can inform the pet owner 12 if all of the pet food in the feeding device 22 or the feeding bowl of the feeding device 23 is consumed or if the amount of pet food remaining therein is less than a predetermined threshold. The cloud database 23 can use text messages, SMS messages, voicemail messages, emails, a website, and the like for such communications with the terminal device 24 of the pet owner 12.

As yet another example of functionality of the cloud database 23, the feeding device 22 can comprise an infrared sensor that detects how often the pet 11 approaches the feeding device 22. The pet 11 approaching the feeding device 22 can be indicative of the eating desire of the pet 11. The cloud database 23 can receive the eating desire data from the feeding device 22 and provide the eating desire data to the terminal device 24 of the pet owner 12. The feeding device 22 can comprise a camera, and pictures from the camera can be received by the cloud database 23 and provided by the cloud database 23 to the terminal device 24 of the pet owner 12.

In an embodiment, the cloud database 23 can communicate with additional devices 25, such feeding devices and/or terminal devices of pet owners other than the pet owner 12. Preferably the cloud database 23 communicates with the additional devices 25 using the internet. For example, the other pet owners having the additional devices 25 can own the same type of pet as the pet 11 of the pet owner 12, and the pet owners having the same type of pet can form a consumer-club. The same type of pet can be determined at least partially based on a criterion that is the species, such as dog or cat; the breed of the pet; the age of the pet; and/or the weight of the pet.

The cloud database 23 can aggregate and can store the data for the type of pet from the additional devices 25. The cloud database 23 can use the aggregated data to assist the pet owners having the same type of pet. In an embodiment, the analysis of the real-time health and wellness measurements, the eating desire data, and the food consumption data of the pet 11 by the cloud database 23 can use the aggregated data of other pets that are the same type of pet. For example, the analysis by the cloud database 23 can use the health and wellness measurements, the eating desire data, and/or the food consumption data of the other pets that are the same type of pet as the pet 11.

The terminal device 24 can use the wireless connection 34 to send inquiries and/or commands to the feeding device 22. In an embodiment, the feeding device 22 can store one or more pre-recorded audio recordings and can play a selected audio recording in response to a command from the terminal device 22. For example, the feeding device 22 can store a pre-recorded voice recording of the pet owner 12 and can play the voice recording to call and train a young pet for feeding. As another example, the feeding device 22 can play audio spoken into the terminal device 24 by the pet owner 12 substantially concurrently.

Figure 2:
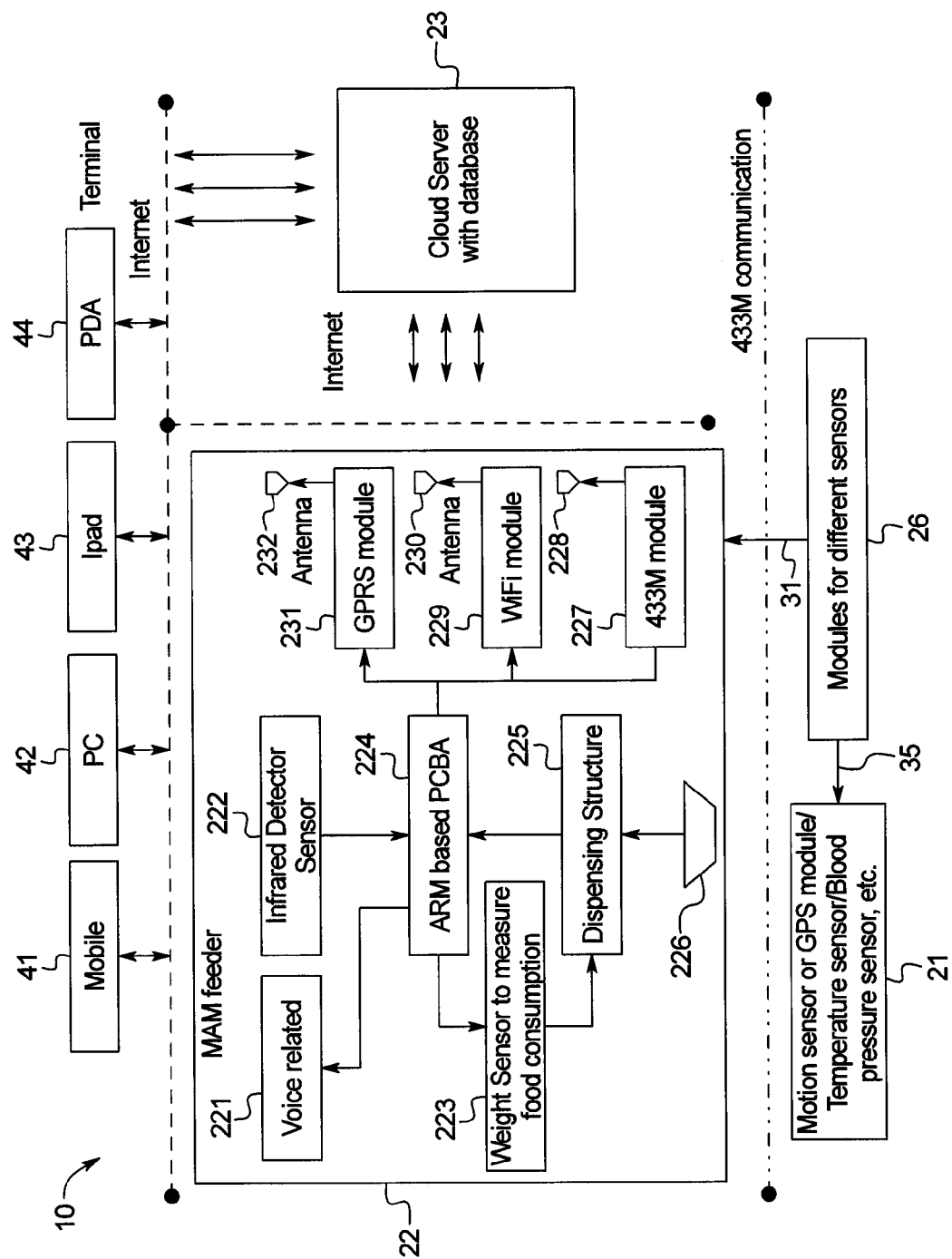
FIG. 2 is a schematic diagram of an embodiment of a pet monitoring and feeding system provided by the present disclosure.

FIG. 2 schematically illustrates an embodiment of the system 10. As shown in FIG. 2, the terminal device 24 of the pet owner 12 can be at least one of a mobile telephone 41, such as a smartphone; a laptop or desktop personal computer 42; a tablet 43; or a personal digital assistant 44. These devices can communicate bidirectionally with the feeding device 22 and/or the cloud database 23. The present disclosure is not limited to a specific embodiment of the terminal device 24 of the pet owner 11, and the terminal device 24 can be any device that can access the internet and display a website.

The feeding device 22 can comprise a general packet radio service ("GPRS") module 231 comprising a GRPS antenna 232. Alternatively or additionally, the feeding device 22 can comprise a Wi-Fi module 227 comprising a Wi-Fi antenna 230. The GPRS module 231 and/or the Wi-Fi module 227 can enable the feeding device 22 to connect to the internet to communicate bidirectionally with the terminal device 24 and/or communicate bidirectionally with the cloud database 23. The feeding device 22 can comprise a processor 224, such as a printed circuit board assembly. The GPRS module 231 and/or the Wi-Fi module 227 can provide communications from the cloud database 23 and the terminal device 24 to the processor 224. In an embodiment, the feeding device 22 can connect to the cloud database 23 frequently, for example about every thirty seconds, so as to be considered a real-time communication.

The sensor 21 can automatically communicate directly and wirelessly to the feeding device 22. Alternatively or additionally, the sensor 21 can communicate indirectly with the feeding device 22 using a communication module 26 that receives data from the sensor 21 and sends the data to the feeding device 22. In an embodiment, the sensor 21 and/or the communication module 26 send data to the feeding device 22 using 433 MHz frequency radio waves. For example, the feeding device 22 can comprise a 433 M module 227 comprising a 433 M antenna by which the feeding device 22 can receive data from the sensor 21. The processor 224 can receive data from the 433M module 227, such as the data from the sensor 21. In an embodiment, the sensor 21 can communicate with the feeding device 22 frequently, for example about every thirty seconds, so as to be considered a real-time communication.

The feeding device 22 can comprise a scale 223 associated with a feeding bowl 226. The scale 223 can be communicatively connected to the processor 224 so that the processor 224 can record weight of the pet food in the feeding bowl 226 and/or weight changes of the pet food in the feeding bowl 226 in association with a date and a time. For example, the feeding bowl 226 can be fixedly or removably positioned on the scale 223.

The feeding device 22 can comprise an infrared sensor 222 that detects how often the pet 11 approaches the feeding device 22, and the infrared sensor 222 can be communicatively connected to the processor 224. The processor 224 can generate eating desire data based on how often the pet 11 approaches the feeding device 22. The feeding device 22 can comprise a speaker 221 communicatively connected to the processor 224, and the processor 224 can direct the speaker 221 to play a pre-recorded audio recording or play incoming audio from the terminal device 24 of the pet owner 12.

The feeding device 22 can automatically collect the real-time health and wellness measurements, the eating desire data and the food consumption data during any suitable time intervals. For example, the real-time health and wellness measurements, the eating desire data, and the food consumption data can be collected every second, every minute or every hour for a predetermined amount of time. The cloud database 23 can automatically obtain the real-time health and wellness measurements, the eating desire data, and the food consumption data from the feeding device 22. For example, the feeding device 22 can send the real-time health and wellness measurements, the eating desire data, and the food consumption data to the cloud database 23 when obtained or can store the real-time health and wellness measurements and the food consumption data for sending to the cloud database 23 at a later time. The real-time health and wellness measurements and the food consumption data can then be statistically analyzed by the cloud database 23 to determine pet wellness. A website hosted by the cloud database 23 can be accessed by the terminal device 24 of the pet owner 12 to view the real-time health and wellness measurements, the eating desire data, the food consumption data, and the results of analysis thereof by the cloud database 23.

The feeding device 22 can store pet food separately from the feeding bowl 226 such that the stored pet food is inaccessible to the pet 11. The feeding device 22 can comprise a dispensing structure 225 that dispenses at least a portion of the pet food stored in the feeding device 22 into the feeding bowl 226. The processor 224 can control operation of the dispensing structure 225, such as by controlling the amount of the pet food dispensed and the time at which the pet food is dispensed.

Figure 3:
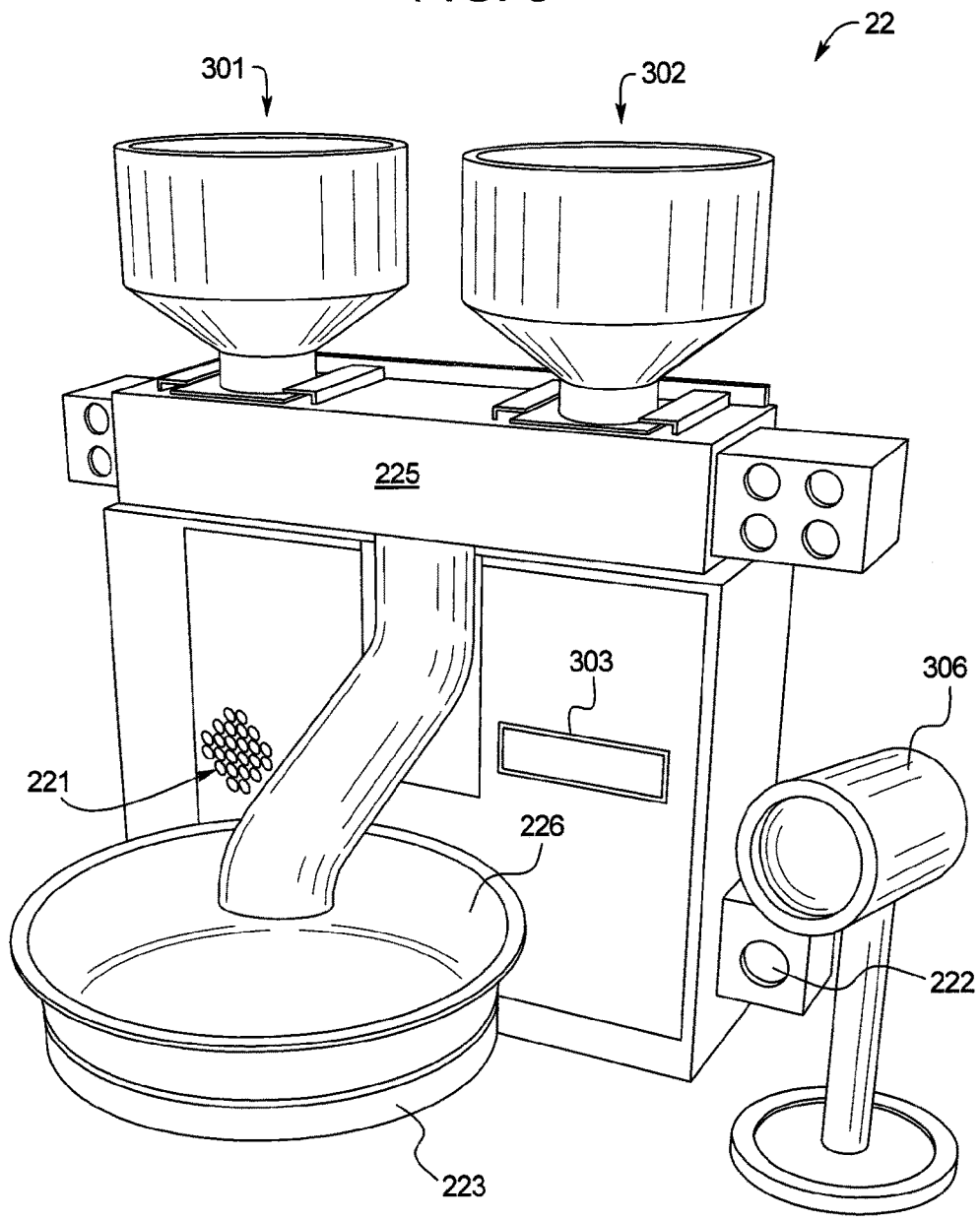
FIG. 3 illustrates an embodiment of a feeding device provided by the present disclosure.

FIG. 3 generally illustrates an embodiment of the feeding device 22. As set forth above, the feeding device 22 can comprise the feeding bowl 226 and the scale 223 associated with the feeding bowl 226. The feeding device 22 can further comprise one or more containers in which pet food is stored separately from the feeding bowl such that the stored pet food is inaccessible to the pet 11. For example, the feeding device 22 can comprise a first container 301 and a second container 302. Each of the containers 301,302 can comprise an inlet, for example a funnel, that can allow pet food to be positioned within the feeding device 22 in a location inaccessible to the pet 11.

The dispensing structure 225 of the feeding device 22 can selectively dispense at least a portion of the pet food stored in one of the containers 301,302 into the feeding bowl 226. The containers 301,302 can contain different types of pet food relative to each other, such as standard pet food and treats respectively, to allow the pet owner 12 and/or the cloud database 23 to control the type of pet food provided to the pet 11 at a given time.

For example, the dispensing structure 225 can dispense at least a portion of the pet food stored in a selected container according to a feeding program established by the pet owner 12 and/or the cloud database 23. The feeding program can specify a plurality of feedings, and each feeding can be associated with a feeding parameter that is at least one of a day, a time, a container, a type of food, and an amount. As another example, the dispensing structure 225 can dispense at least a portion of the pet food stored in a selected container in response to a command received from the cloud database 23 or a command received from the terminal device 24 of the pet owner 12. The command can specify a feeding parameter that is at least one of the day, the time, a container, a type of food, or an amount. In an embodiment, the terminal device 24 can control the dispensing structure 225 using the website hosted by the cloud database 23. In an embodiment, the feeding device 22 dispenses the pet food from the selected container substantially concurrently to receipt of the command by the feeding device 22 and/or input of the command by the pet owner 12 into the terminal device 24, such as within thirty seconds. As yet another example, the dispensing structure 225 can dispense at least a portion of the pet food stored in a selected container in response to a weight of the pet food in the feeding bowl 226 that meets or is below a predetermined threshold.

The feeding device 22 can comprise a display, such as a LCD display, that indicates settings and status for the feeding device 22. For example, the pet owner 12 can manually input at least a portion of the feeding program into the feeding device 22, for example by using an input interface integral with the feeding device 22. The feeding device 22 can display parameters of the manually entered feeding program, can indicate that the feeding program is activated, and/or can indicate that the feeding device 22 is operational.

The feeding device 22 can comprise a camera 306, and pictures or video from the camera 306 can be received by the cloud database 23, stored by the cloud database 23, and/or provided by the cloud database 23 to the terminal device 24 of the pet owner 12. Alternatively or additionally, the feeding device 232 can send the pictures or video directly to the terminal device 24. The camera 306 can capture a picture or video in response to a command from the terminal device 24. In an embodiment, the camera 306 captures the picture or video substantially concurrently to receipt of the command by the feeding device 22 and/or input of the command by the pet owner 12 into the terminal device 24, such as within thirty seconds. The command can be sent from the terminal device 24 directly to the feeding device 22 or indirectly to the feeding device 22 through the cloud database 23. In an embodiment, the camera 306 can automatically capture a picture or video in response to detection of the presence of the pet 11 by the infrared sensor 222.

Figure 4:
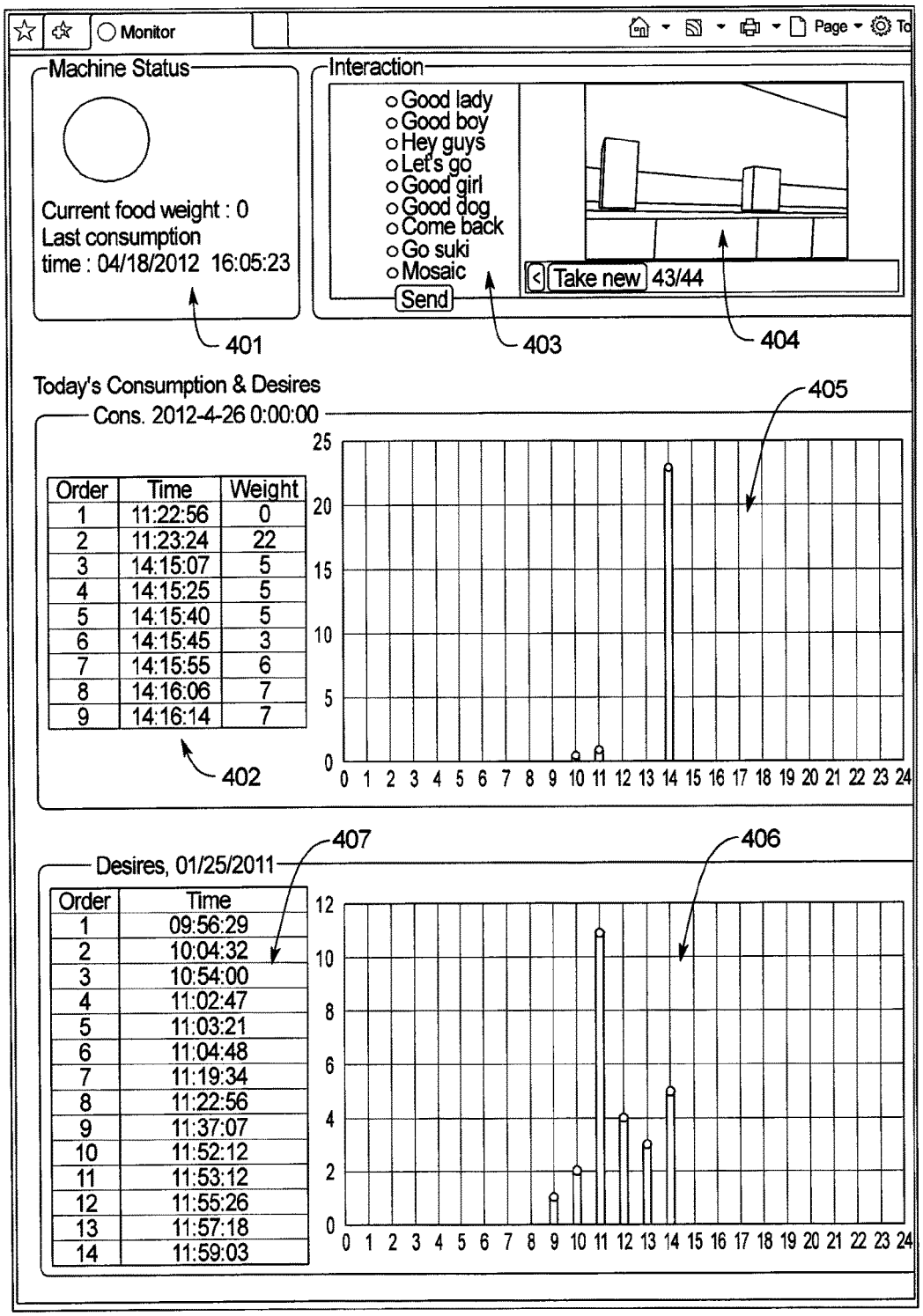
FIG. 4 illustrates an embodiment of a web interface provided by the present disclosure.

FIG. 4 generally illustrates an embodiment of a website 400 hosted by the cloud database 23 and accessible by the terminal device 24. The website 400 can display the status of the feeding device 22, the real-time health and wellness measurements, the eating desire data, the food consumption data, and the results of analysis thereof by the cloud database 23. The website 400 can display a pet activity profile generated from the distances moved by the pet 11 as determined by the sensor 23. In an embodiment, the website 400 can display at least a portion of the health and wellness measurements, the eating desire data, and the food consumption data of the other pets that are the same type of pet as the pet 11.

The website 400 can enable the terminal device 24 to control operation of the feeding device 22. For example, the website 400 can enable the terminal device 24 to enter a command directing dispensation of pet food, and in response to the command the cloud database 23 can send a corresponding message to the feeding device 22. The feeding device 22 can dispense an amount of pet food from a selected container in response to the message from the cloud database. As another example, the website 400 can enable the terminal device 24 to generate a customized feeding program and/or adjust a previously established feeding program. The feeding program can specify a plurality of feedings, and each feeding can be associated with a feeding parameter that is at least one of a day, a time, a container, a type of food, or an amount.

In an embodiment, the website 400 can comprise a device status window 401. The device status window 401 can indicate whether the feeding device 22 is operational or not; as shown in FIG. 4, the device status window 401 can have an icon, such as a circle, that can identify the status based on color. For example, the icon can be grey if the feeding device 22 is off-line and can be green if the feeding device 22 is on-line and can be programmed and/or controlled remotely. The device status window 401 can indicate the current weight of the pet food in the feeding bowl 226 as determined by the scale 223. The device status window 401 can identify the day and the time when the pet 11 most recently ate as indicated by the most recent change in weight of the pet food in the feeding bowl 226 as determined by the scale 223.

In an embodiment, the website 400 can comprise audio controls 403. The audio controls 403 can comprise a list of pre-recorded audio recordings, and the pet owner 12 can use the terminal device 24 to select one of the pre-recorded audio recordings. The feeding device 24 can use the speaker 221 to play the selected audio recording when the pet owner 12 uses the terminal device 24 to select a "send" icon provided by the website 400. The feeding device 24 can play the selected audio recording substantially concurrently to the pet owner 12 selecting the "send" icon, such as within thirty seconds.

The website 400 can comprise a visual window 404 that displays the pictures or video captured by the camera 306 of the feeding device 22. The camera 306 can capture a new picture or video in response to the pet owner 12 using the terminal device 24 to select a "take new" icon provided by the website 400. The website 400 can enable the pet owner 12 to view previously captured pictures or video stored by the cloud database 23.

The website 400 can display the feeding consumption data as text 402. For example, the feeding consumption text 402 can list the dates and/or times of consumption and the amount of pet food consumed at each time. Additionally or alternatively, the website 400 can display the feeding consumption data as a graph 402. For example, the feeding consumption graph 402 can have the consumption date and/or time as the x-axis and the amount of pet food consumed at each time as the y-axis.

The website 400 can display the eating desire data as text 407. For example, the eating desire text 407 can list the times that the pet 11 approached the feeding device 22 and the amount of time spent by the feeding device 22 during each approach. As another example, the eating desire text 407 can list the time that the pet 11 spent proximate to the feeding device 22 for each day of a predetermined time period. Additionally or alternatively, the website 400 can display the eating desire data as a graph 406. For example, the eating desire graph 406 can have the time that the pet 11 approached the feeding device 22 as the x-axis and the amount of time spent by the feeding device 22 during each approach as the y-axis. As another example, the eating desire graph 406 can have the dates as the x-axis and the amount of time spent by the feeding device 22 during each day as the y-axis.

In another aspect, the present disclosure provides a method of remotely monitoring and feeding a pet. The method comprises automatically measuring pet food consumption locally; automatically obtaining real-time pet health and wellness measurements locally, such as body conditions and an amount of movement of the pet; and transmitting the pet food consumption data and the real-time health and wellness measurements to a remote location. In an embodiment, the method comprises automatically obtaining eating desire data locally, such as the times that the pet approaches a feeding bowl, and transmitting the eating desire data to the remote location. In an embodiment, the method comprises and transmitting the real-time pet health and wellness measurements to the remote location.

The pet food consumption data, the eating desire data, and/or the real-time pet health and wellness measurements can be analyzed at the remote location. Based on the analysis and/or scientific knowledge stored at the remote location, feeding suggestions and/or a customized feeding program can be generated. At least a portion of the real-time health and wellness measurements, the eating desire data, the food consumption data, and the results of analysis thereof can be provided to a terminal device of the pet owner, for example by a website accessible to the terminal device. In an embodiment, the terminal device can input commands and/or inquires into the website to control local feeding of the pet. In an embodiment, the method comprises transmitting at least a portion of the real-time health and wellness measurements, the eating desire data, and the food consumption data obtained locally directly to the terminal device of the pet owner.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system comprising:
a portable sensor that obtains a measurement related to health of a pet; and
a feeding device to which the portable sensor is wirelessly communicatively connected, the feeding device configured for receiving the measurement related to the health of the pet from the portable sensor, the feeding device comprising a scale, a first container comprising a first inlet, a second container comprising a second inlet, a bowl positioned on the scale, and a dispenser, wherein the dispenser is mechanically connected to the first container at the first inlet, mechanically connected to the second container at the second inlet, and configured to respectively guide a first food from the first container and a second food from the second container into the bowl positioned on the scale, the feeding device configured for generating feeding consumption data, and the feeding device further comprises a wireless connection module configured to connect to the internet.

2. The system of claim 1, the feeding device further comprising a transmission device configured to send a transmission of the measurement related to the health of the pet and the feeding consumption data using the internet connection; and the system further comprising a database remotely located relative to the feeding device, the database configured to receive the transmission of the measurement related to the health of the pet and the feeding consumption data through the internet connection from the transmission device.

3. The system of claim 2 further comprising a computing device configured to access the database, wherein the computing device is further configured to perform an analysis of the measurement related to the health of the pet and the feeding consumption data using information stored in the database, and the information stored in the database is selected from the group consisting of scientific information, previously compiled data for the pet, previously compiled data for other pets that are the same type of pet, and a combination thereof.

4. The system of claim 3 wherein the database hosts a website comprising a user input interface that provides at least a portion of the measurement related to the health of the pet, the feeding consumption data, and a result of the analysis, and the database is further configured to transmit a command to the feeding device in response to a user input into the user input interface.

5. The system of claim 1 wherein the portable sensor is selected from the group consisting of a GPS system, a real-time temperature sensor, a real-time blood pressure sensor, a real-time heart rate sensor, and combinations thereof.

* * * * *